(12) United States Patent
Spindler

(10) Patent No.: US 11,213,661 B2
(45) Date of Patent: Jan. 4, 2022

(54) EXPANDABLE MEDICAL DEVICE AND METHOD OF USE THEREOF

(71) Applicant: COOK MEDICAL TECHNOLOGIES LLC, Bloomington, IN (US)

(72) Inventor: Ralf Spindler, Solsberry, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 509 days.

(21) Appl. No.: 16/229,095

(22) Filed: Dec. 21, 2018

(65) Prior Publication Data

US 2019/0209814 A1     Jul. 11, 2019

Related U.S. Application Data

(60) Provisional application No. 62/613,923, filed on Jan. 5, 2018.

(51) Int. Cl.
*A61M 25/10* (2013.01)
*A61L 29/16* (2006.01)
(Continued)

(52) U.S. Cl.
CPC ..... *A61M 25/104* (2013.01); *A61B 17/12136* (2013.01); *A61L 29/041* (2013.01); *A61L 29/085* (2013.01); *A61L 29/14* (2013.01); *A61L 29/16* (2013.01); *A61L 31/048* (2013.01); *A61L 31/10* (2013.01); *A61L 31/14* (2013.01);
(Continued)

(58) Field of Classification Search
CPC .......... A61L 29/14; A61L 29/16; A61L 31/14; A61L 31/16; A61B 17/12136; A61M 2025/0024; A61M 2025/105; A61M 2025/1086; A61M 25/1002; A61M 25/104; A61M 25/00; A61M 25/10; A61M 2025/1043
See application file for complete search history.

(56) References Cited

U.S. PATENT DOCUMENTS

| 4,950,258 A | 8/1990 | Kawai et al. |
| 5,603,722 A | 2/1997 | Phan et al. |

(Continued)

FOREIGN PATENT DOCUMENTS

| WO | WO 95/24939 A1 | 9/1995 |
| WO | WO 2007/145800 A2 | 12/2007 |
| WO | WO 2009/124231 A1 | 10/2009 |

OTHER PUBLICATIONS

Marc Behl et al., "Shape-Memory Polymers", MaterialsToday Apr. 2007, vol. 10, No. 4, ISSN: 1369 7021 © Elsevier Ltd 2007, 9 pgs.
(Continued)

*Primary Examiner* — Jason E Flick
(74) *Attorney, Agent, or Firm* — Crowell & Moring LLP

(57) ABSTRACT

The present invention relates generally to expandable medical devices including a light-activated shape-memory polymer. In certain embodiments, the devices include, for example, balloon catheters, used to treat narrowed or obstructed portions of a body vessel, and retrieval devices, used to remove obstructions from a body vessel. Certain aspects of the invention relate to methods of manufacturing and using such devices.

14 Claims, 6 Drawing Sheets

(51) Int. Cl.
    *A61L 31/10*     (2006.01)
    *A61L 29/14*     (2006.01)
    *A61L 29/04*     (2006.01)
    *A61L 31/14*     (2006.01)
    *A61L 31/16*     (2006.01)
    *A61L 29/08*     (2006.01)
    *A61L 31/04*     (2006.01)
    *A61B 17/12*     (2006.01)
    *A61M 25/00*     (2006.01)

(52) U.S. Cl.
    CPC ......... *A61L 31/16* (2013.01); *A61M 25/1002* (2013.01); *A61L 2300/416* (2013.01); *A61M 2025/0024* (2013.01); *A61M 2025/105* (2013.01); *A61M 2025/1086* (2013.01)

(56) References Cited

U.S. PATENT DOCUMENTS

| | | |
|---|---|---|
| 6,350,271 B1 | 2/2002 | Kurz et al. |
| 6,485,512 B1 | 11/2002 | Cheng |
| 7,744,604 B2 | 6/2010 | Maitland et al. |
| 8,449,592 B2 | 5/2013 | Wilson et al. |
| 2003/0236533 A1 | 12/2003 | Wilson et al. |
| 2004/0034405 A1 | 2/2004 | Dickson |
| 2004/0111111 A1 | 6/2004 | Lin |
| 2005/0228417 A1 | 10/2005 | Teitelbaum |
| 2007/0129784 A1 | 6/2007 | Lendlein et al. |
| 2007/0299456 A1* | 12/2007 | Teague ................ A61B 17/221 606/127 |
| 2011/0190683 A1 | 8/2011 | Gellman et al. |

OTHER PUBLICATIONS

Wayne Francis et al., "Spiropyran Based Hydrogels Actuators—Walking in the Light", Sensors and Actuators B 250 (2017) 608-616.

Dmitri A. Ossipov et al., "Light-Activatable Prodrugs Based on Hyaluronic Acid Biomaterials" Carbohydrate Polymers 180 (2018) 145-155.

Florence Pilate et al., "Shape-Memory Polymers for Multiple Applications in the Materials World", European Polymer Journal 80 (2016) 268-294.

Gayong Shim et al., "Light-Switchable Systems for Remotely Controlled Drug Delivery", Journal of Controlled Release (2017), http://dx.doi.org/10.1016/i.iconrel.2017.09.009.

J.S. Sodhi et al., "Inhomogeneous Deformations of Light Activated Shape Memory Polymers", International Journal of Engineering Science 89 (2015) 1-17.

Ward Small, IV, et al., "Laser-Activated Shape Memory Polymer Intravascular Thrombectomy Device", Oct. 3, 2005 / vol. 13, No. 20 / Optics Express 8204, 10 pgs.

European Search Report for corresponding EP 19150415, dated Jun. 6, 2019, 7 pages.

* cited by examiner

FIG. 2A
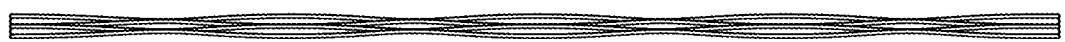
FIG. 2B
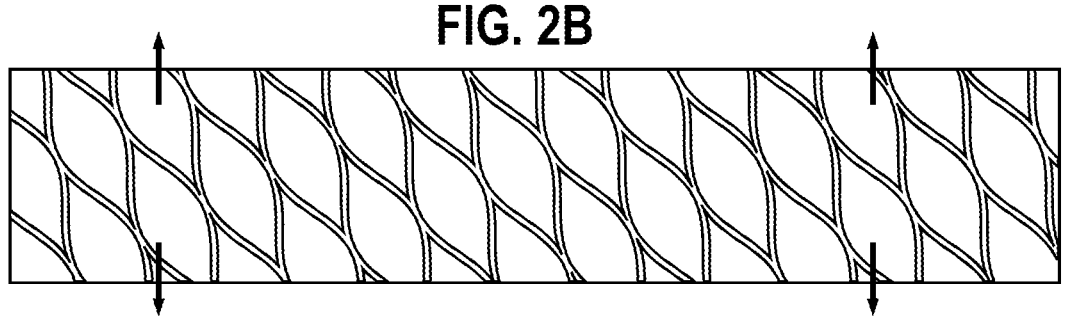
FIG. 3A          FIG. 3B
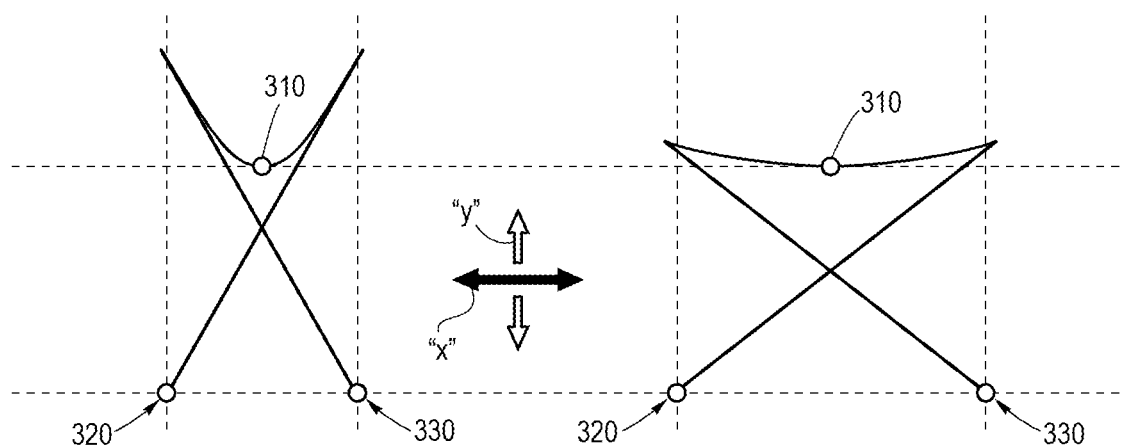

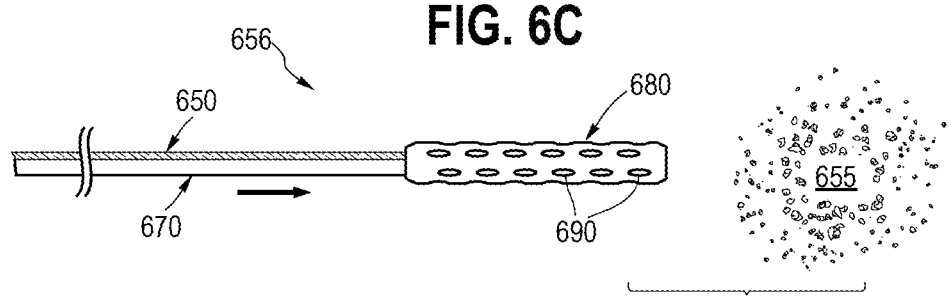
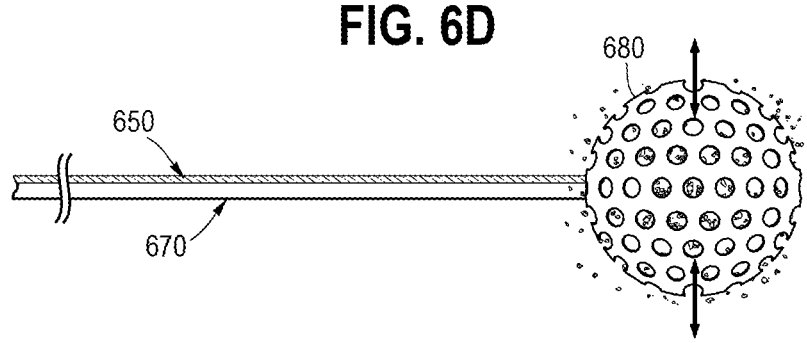
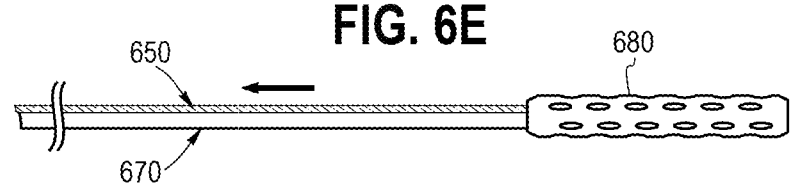

EXPANDABLE MEDICAL DEVICE AND METHOD OF USE THEREOF

RELATED APPLICATIONS

This application claims the benefit of priority of U.S. Provisional application Ser. No. 62/613,923 filed on Jan. 5, 2018, which application is incorporated by reference herein in its entirety.

TECHNICAL

The present invention relates generally to expandable medical devices including a light-activated shape-memory polymer. In certain embodiments, the devices include balloon catheters, used to treat narrowed or obstructed portions of a body vessel, and retrieval devices, used to remove obstructions from a body vessel. Certain aspects of the invention relate to methods of manufacturing and using such devices.

BACKGROUND

Implantable medical devices, particularly expandable endoluminally deployable medical devices, are known for a variety of medical applications. For example, balloon catheters are widely used in the medical profession for various intraluminal procedures. One common procedure involving the use of a balloon catheter relates to angioplasty dilation of coronary or other arteries suffering from stenosis (i.e., a narrowing of the arterial lumen that restricts blood flow). For example, balloon catheters can have application in the treatment of blockages of the peripheral blood vessels, esophagus, trachea, colon, biliary tract, urinary tract and at other locations in the body. Other applications include the treatment of carotid artery stenosis, the narrowing of the carotid arteries, which are the main arteries in the neck that supply blood to the brain. Carotid artery stenosis (also called carotid artery disease) is a relatively high risk factor for ischemic stroke.

Although balloon catheters are used in many other procedures as well, coronary angioplasty using a balloon catheter has drawn particular attention from the medical community because of the growing number of people suffering from heart problems associated with stenosis. This has led to an increased demand for medical procedures to treat such problems. Angioplasty procedures have become a popular alternative for treating coronary stenosis because angioplasty procedures are considerably less invasive than other alternatives. For example, stenosis of the coronary arteries has traditionally been treated with bypass surgery. In general, bypass surgery involves splitting the chest bone to open the chest cavity and grafting a replacement vessel onto the heart to bypass the blocked, or stenosed, artery. However, coronary bypass surgery is a very invasive procedure that is risky and requires a long recovery time for the patient.

To address the increased need for coronary and peripheral artery treatments, the medical community has turned to angioplasty procedures, in combination with stenting procedures, to avoid the problems associated with traditional bypass surgery. Typically, angioplasty procedures are performed using a balloon-tipped catheter that may or may not have a stent mounted on the balloon. The physician performs the angioplasty procedure by introducing the balloon catheter into a peripheral artery (commonly one of the leg arteries) and threading the catheter to the narrowed part of the coronary artery to be treated. During this stage, the balloon is deflated and collapsed onto the shaft of the catheter in order to present a low profile which may be passed through the arterial lumens.

Once the balloon is positioned at the narrowed part of the artery, the balloon is expanded by pumping a mixture of saline and contrast solution through the catheter to the balloon. As a result, the balloon presses against the inner wall of the artery to dilate it. If a stent is mounted on the balloon, the balloon inflation also serves to expand the stent and implant it within the artery. After the artery is dilated, the balloon is deflated so that it once again collapses onto the shaft of the catheter. The balloon-tipped catheter is then retracted from the arteries. If a stent is mounted on the balloon of the catheter, the stent is left permanently implanted in its expanded state at the desired location in the artery to provide a support structure that prevents the artery from collapsing back to its pre-dilated condition. On the other hand, if the balloon catheter is not adapted for delivery of a stent, either a balloon-expandable stent or a self-expandable stent may be implanted in the dilated region in a follow-up procedure.

Although the treatment of stenosed coronary arteries is one common example where balloon catheters have been used, many other uses are also possible. For example, balloon catheters can have application in the treatment of blockages of the peripheral blood vessels, esophagus, trachea, colon, biliary tract, urinary tract and at other locations in the body. Other applications include the treatment of carotid artery stenosis, the narrowing of the carotid arteries, which are the main arteries in the neck that supply blood to the brain. Carotid artery stenosis (also called carotid artery disease) is a relatively high risk factor for ischemic stroke. The narrowing is usually caused by plaque build-up in the carotid artery. Plaque forms when cholesterol, fat and other substances form in the inner lining of an artery. This formation is called atherosclerosis.

Another application of expandable devices is in the removal of solid masses from body vessels. Certain body vessels that transport fluids are subject to obstruction by solid masses, or "stones", formed from crystals that separate from the transported fluid and build up within the duct. Examples of such masses include renal stones, gall stones and gastric stones. For example, urinary stone prevalence is estimated at 3% in all individuals, and it affects up to 12% of the population during their lifetime. Urinary stone recurrence rates approach 50% at 10 years and white males have the highest incidence in the U.S. In many instances, such masses pass out of the body without the need for intervention by a physician. However, large stones that cause lasting symptoms or other complications require intervention to remove the stones from the body.

Renal stones are one of the most painful of urologic disorders. Such stones form within the kidney from crystals that separate from urine. Sometimes, such stones travel down the urinary tract and are expelled from the body. In other cases, a stone may cause a blockage in the urinary tract. The removal of urinary stones is currently done for large stones.

Extracorporeal shock wave lithotripsy ("ESWL") is a minimally invasive treatment for the treatment of renal and gallbladder stones. In ESWL, ultrasonic sound waves that are created outside the body travel through the skin and body tissues until they hit the denser stones. The stones break down into smaller particles that can sometimes be expelled naturally from the body. Renal stones can also be removed using laser lithotripsy. This technique involves the insertion of a probe into the renal track. A cystoscope or ureteroscope is inserted into the patient's urethra, either directly or over a guide wire, and is advanced up the urinary tract to locate the target renal stone. Once the stone is located, a thin fiber optic is introduced into a channel of the endoscope and advanced until it comes into contact with the stone. Light from a laser, for example, a holmium laser, is directed through the fiber optic and the stone disintegrates or fragments.

One problem of the techniques that break up stones is that small stone fragments often remain in vivo after the treatment. Certain retrieval techniques may allow for the retrieval of larger stone fragments. However, which increases the risk of regrowth of stones.

SUMMARY

The present invention is generally related to an implantable medical device having an expandable portion and to methods of preparing and using such a device. The device may be, for example, a balloon, a stent, a stent graft or a retrieval device. In one embodiment, the device includes an elongated catheter including a lumen extending from a distal end to a proximal end of the catheter. An expandable body, preferably including a light-sensitive polymeric material, attaches to the distal end of the elongated catheter. At least one optical fiber extends within the lumen and has a distal end optically coupled to the light-sensitive polymeric material and a proximal end optically coupled to a light source. The light source may be, for example, a laser or a light emitting diode.

The expandable body has an expanded configuration and a collapsed configuration and transitions from the collapsed configuration to the expanded configuration upon optical illumination of the light-sensitive polymeric material. In certain embodiments, the light-sensitive polymeric material includes a polymer coupled cinnamic acid or cinnamylidene acetic acid.

The expandable body may include a hollow tubular body having a tubular wall containing the light-sensitive polymeric material and defining an internal lumen. In certain embodiments, the tubular wall includes of plurality of interconnected segments, where each segment includes a node point containing the light-sensitive polymeric material. In one embodiment, at least one of the interconnected segments has an expanded configuration and a collapsed configuration. Transition from the collapsed configuration to the expanded configuration occurs upon illumination of the light-sensitive polymeric material. In some embodiments, the transition includes lengthening of the segment in a first direction without a change in dimension is a second perpendicular dimension. In another embodiment, the expandable body includes a plurality of holes. At least one of the holes may increase in size upon expansion of the expandable body. In yet another embodiment, the elongated catheter includes a second lumen.

Another aspect of the invention provides a kit including an implantable medical device as disclosed herein and a retrieval basket, where a distal portion of the retrieval basket is sized to slidably extend within a lumen of the elongated catheter.

Yet another aspect of the invention provides a method of removing an obstruction from a region of a body vessel. In one embodiment, the method includes fragmenting the obstruction to form fragments of the obstruction. The method also includes placing the distal end of a medical device as described herein in the region of the body vessel containing the fragments and expanding the hollow expandable body by illuminating a proximal end of the plurality of optical fibers with a light source. Upon expansion of the hollow expandable body, the plurality of fragments are positioned within the lumen of the body. The distal end of a flushing tube is advanced into a body lumen of the hollow expandable body and the fragments are aspirated from the vessel through the flushing tube.

In some embodiments, the method also includes positing the basket of a retrieval device in a region containing the fragments and removing the larger fragments before the smaller fragments are aspirated from the vessel. The vessel may be, for example, a vessel of the urinary system and the obstruction may be, for example, a kidney stone. The fragmenting may be performed using an method such as laser illumination, sound wave illumination, percutaneous nephrolithotomy or the use of an ureterscope.

In one embodiment, expanding the hollow expandable body results in expansion of the pore size of the plurality of pores. In another embodiment, the light-sensitive polymeric material includes a polymer coupled to a material such as cinnamic acid or cinnamylidene acetic acid.

BRIEF DESCRIPTION OF THE DRAWINGS

Embodiments of the present invention are described below, by way of example only, with reference to the accompanying drawings, in which:

FIGS. 1(A-B) are schematic illustrations showing one embodiment an expandable device. In this embodiment, the device includes straight segments.

FIGS. 2(A-B) are schematic illustrations showing one embodiment an expandable device. In this embodiment, the device includes tilted segments.

FIGS. 3(A-B) are schematic illustrations showing a device that is expandable in one dimension without changing size is a second perpendicular direction. In FIG. 3(A) the segments are in the contracted state. In FIG. 3(B) the segments are shown in an expanded state FIGS. 4(A-C) are schematic illustrations showing one embodiment an expandable device incorporating multiple expandable segments that are expandable in one direction.

FIGS. 5(A-B) are schematic illustrations showing an expandable device having a number of pores.

DESCRIPTION OF THE PREFERRED EMBODIMENTS

Figure 1A:
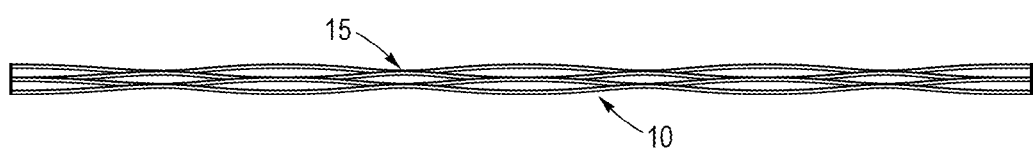
In FIG. 1(A) the segments are in the contracted state.

It is to be understood that the drawings are schematic only and not to scale. Often only the principal components relevant to the teachings herein are shown in the drawings, for the sake of clarity.

The term "implantable medical device" refers to a medical device that is either permanently or temporarily inserted into a patient's body for treatment of a medical condition.

The term "therapeutic effect" as used herein means an effect which induces, ameliorates or otherwise causes an improvement in the pathological symptoms, disease progression or physiological conditions associated with or resistance to succumbing to a disorder, for example restenosis, of a human or veterinary patient. The term "therapeutically effective amount" as used with respect to a drug means an amount of the drug which imparts a therapeutic effect to the human or veterinary patient.

Implantable Devices Incorporating Shape-Memory Polymers

One aspect of the present invention provides an implantable medical device incorporating an expandable region including a shape-memory polymer ("SMP"). In one embodiment, the SMP is a light-activated shape-memory polymer ("LASMP"). The device may also include a light source, for example a laser or a LED, optically connected to the LASMP by a light path, such as an optical fiber. In another embodiment the states of the light source (on, off) determine the conformational state of the LASMP.

The device may be any implantable device including an expandable portion, for example, a stent, a coil, a stent-graft, an expandable filter, a balloon, a cutting balloon, a scoring balloon, a weeping (perfusion) balloon, or any combination of these devices. In one preferred embodiment, the change in the conformational state of the LASMP results in a change in the physical dimension of the medical device. For example, the device many transform from a collapsed to an expanded state upon illumination of the LASMP. Of course, the present embodiments also include those in which the device transforms from an expanded to a collapsed state upon illumination of the LASMP. Such devices can be used in place of conventional expandable devices such as, for example, stents, stent-grafts or balloon catheters.

The use of light as stimulus to actuate the LASMPs presents several advantages over, for example, the heating stimulus approach. Activation of LASMP materials can be executed for biomedical applications while avoiding undesirable heating/burning of the device or surrounding tissue during actuation. Another advantage is that control or multiple configurations (states) may be obtained at room temperature by selecting suitable wavelength, light polarization direction and intensity. In some embodiments, multiple light paths (for example multiple optical fibers) may extend from one or more light sources to different regions of the device. Such a configuration allows different regions containing LASMP material to be illuminated at different times and for controlled transition of different parts of the device.

Polymer shape-changes, such as contraction and bending, have been observed in nematic liquid-crystal elastomers containing azobenzene moieties for their trans-cis photo-isomerization. In certain embodiments, a photoresponsive change in shape is obtained due the presence of photosensitive functional groups along the chain of the polymer material. For example, cinnamic acid (CA), or cinnamylidene acetic acid (CAA) may be utilized as photoresponsive switches. These materials undergo photo-reversible [2+2] cycloaddition reaction at a certain wavelength. Cyclobutane rings occur by dimerization of the double bonds from two neighbor molecules upon UV light irradiation with specific wavelength (k<260 nm and 300 nm for CA and CAA, respectively). The reverse reaction occurs at k<260 nm for both moieties.

For example, when coiled segments of polymer chains having such a derivation are elongated by stretching the polymer, new cross-links in the material may be formed upon irradiation and the temporary shape is finally obtained after unloading. This concept has been shown to be the basis for the production of one LASMP system in which CA molecules grafted onto the polymer network made of n-butyl acrylate (BA), hydroxyethyl methacrylate (HEMA) and ethylene glycol-1-acrylate-2-CA (HEA-CA) with (propylene glycol) dimethacrylate as cross-linker.

In another embodiment, an interpenetrated network (IPN) made of n-butyl acrylate is loaded with about 20 wt % star-poly(ethylene-glycol) containing CAA end-groups. In yet another embodiment, a diol monomer with a pendant photo-responsive group, i.e. N,N-bis-2-(hydroxyethyl)cinnamide (BHECA), is subjected to a two-step condensation reaction using low molecular weight PCL-diol [PCL(OH)$_2$] and poly(L,L-lactide)-diol [PLLA(OH)$_2$] leading to a PUR multiblock of biodegradable segments and pendant photo-reactive groups. A permanent network is achieved by physical cross-linking through hard phase of PUR (PLLA). Further example of LSSMPs are described, for example, in Pilate, F. et al. "Shape-memory Polymers for Multiple Applications in the Materials world" European Polymer Journal, 80 (2016) pp. 268-294.

In yet another embodiment, the LASMP is a photosensitive crosslinked hyaluronan hydrogel incorporating heterobifunctional linkers with middle photo-labile ortho-nitrobenzyl group and orthogonally reactive terminals. Methods preparing such materials are described in Ossipov, Dmitri A. et al. "Light-activatable prodrugs based on hyaluronic biomaterials" Carbohydrate Polymers 180 (2018) 145-155.

In another embodiment, the LASMP is a photpsensitive hydrogel based on N-isopropylacrylamide-co-acrylated spiropyran-co-acrylic acid p(NIPAAm-co-SP-co-AA). The presence of the photochromic spiropyran molecule in the polymer structure causes these hydrogels reversibly shrink and swell in aqueous environments when exposed to different light conditions. Methods of preparing such materials are described in Wayne Francis et al., "Spiropyran based hydrogels actuators—Walking in the light", Sensors and Actuators B 250 (2017) 608-616.

Other materials suitable for use in the present embodiments include hydrogels based on poly(N-isopropylacrylamide ("NIPAAm"), N,N' methylene-bis(acrylamide) ("MBis"), spiropyran based hydrogels (e.g. SPA-8), phenyl-bis(2,4,6-trimethyl benzoyl) phosphine oxide ("PBPO") and Acrylic acid based hydrogeld ("AA").

In general, LASMPs utilize processes of photo-crosslinking and photo-cleaving to change state of the molecule. In one embodiment, photo-crosslinking is achieved by using one wavelength of light, while a second wavelength of light reversibly cleaves the photo-crosslinked bonds. The effect achieved results in a material that may be reversibly switched between, for example, an elastomer and a rigid polymer. The incident light does not change the temperature of the polymer, only the cross-linking density within the material. For example, it has been reported that such polymers containing cinnamic groups can be fixed into predetermined shapes by UV light illumination (>260 nm) and then recover their original shape when exposed to UV light of a different wavelength (<260 nm). Examples of such photo-responsive switches include cinnamic acid and cinnamylidene acetic acid.

Figure 1B:
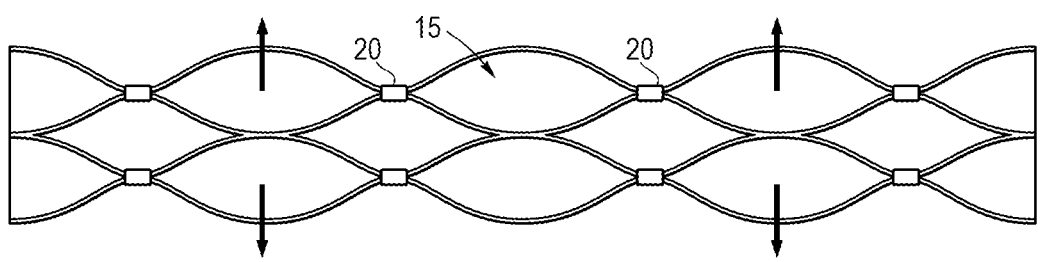
In FIG. 1(B) the segments are shown in an expanded state.

Turning now to FIGS. 1(A) and 1(B). FIGS. 1(A-B) are schematic illustrations showing one embodiment an expandable device of the present invention. In this embodiment, expandable portion 10 is formed of interconnected segments 15 including node points 20. The node points at least one light-sensitive polymeric material, for example, one of the LASMP materials disclosed herein. In FIG. 1(A) the device is illustrated in a collapsed configuration. In one embodiment, the device is in this configuration in the absence of illumination of the LASMP. FIG. 1(B) illustrates the device in an expanded configuration, i.e. in the presence of illumination of the LASMP. In one embodiment, when the light is extinguished, the device will revert to the collapsed configuration.

FIGS. 2(A) and 2(B) show another embodiment of such an expandable device. Again, In FIG. 2(A) the device is illustrated in a collapsed configuration, while FIG. 2(B) illustrates the expanded configuration. In FIGS. 1(A-B), the segments are generally eye-shaped and are aligned with the direction of extension of the device. However, the FIGS. 2(A-B), the segments are aligned at an angle (tilted) with respect to the direction of expansion of the device. In certain embodiments, the tilted configuration may offer advantages in that a higher radial force is generated upon expansion of the device.

Turning now to FIGS. 3(A-B). In some embodiments, expansion of a device, such as a stent or stent graft, in a radial dimension may be required while maintaining a constant length. FIG. 3(A-B) illustrate one embodiment of how such a limited expansion of the device may be achieved. In FIG. 3(A), the device is illustrated in a contracted state in the "X" axis. In FIG. 3(B), the device is illustrated in an expanded configuration in the "X" axis. Here, the distance between nodes 320 and 330 increased due to a change in the state of node 310. For example, node 310 may be illuminated by light to change the state of the LASMP at this node.

Figure 4A:
In FIG. 4(A) the segments are in the contracted state.
Figure 4B:
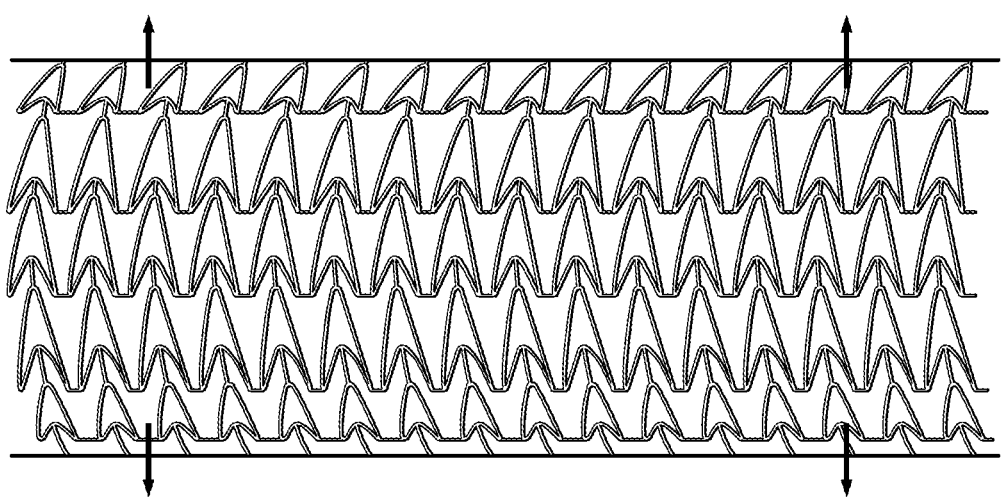
In FIG. 4(B) the segments are shown in an expanded state.

However, such a change of configuration does not change the distance between nodes 320/330 and node 310. FIGS. 4(A-B) are schematic illustrations showing one embodiment an expandable device incorporating multiple expandable segments that are expandable in one direction. In FIG. 4(A) the segments are in the contracted state. In FIG. 4(B) the segments are shown in an expanded state.

Figure 4C:
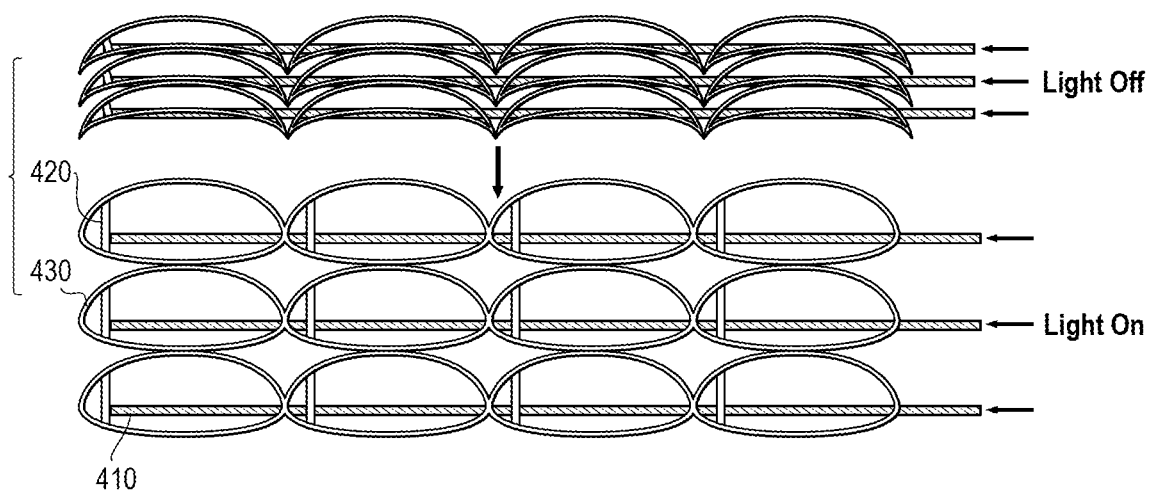
In FIG. 4(C) a string-like or stretching LASMP stretches an elastic polymer region when illuminated.

FIG. 4(C) illustrates another embodiment on a light activated expansion. Here elastic polymer or metal segments 430, illustrated here a oval segments, are expanded by LASMP actuators 420 when the actuators are illuminated by light delivered at fiber optics 410.

Figure 5A:
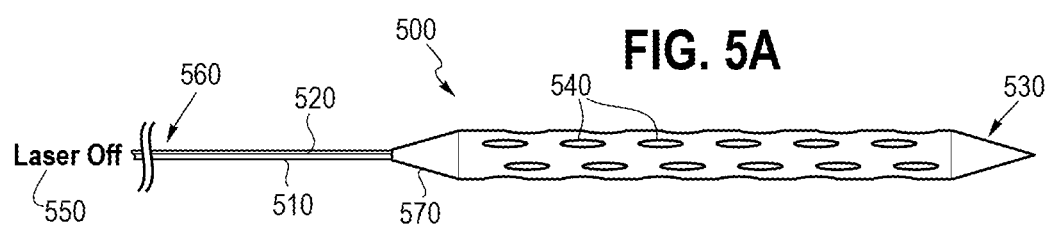
In FIG. 5(A) the device is shown in a contracted state.
Figure 5B:
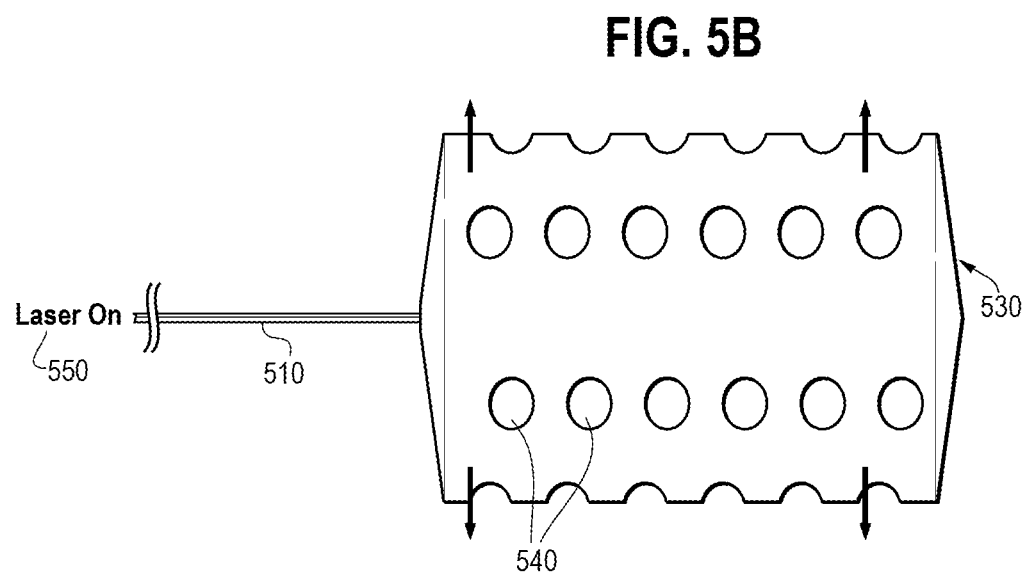
In FIG. 5(B) the device is shown in an expanded state.

Turning now to FIGS. 5(A-B). FIGS. 5(A-B) are schematic illustrations showing an expandable device 500, which may include a number of holes 540. As will be illustrated in more detail below, such devices have found application in retrieving fragments of an obstruction from a vessel of a patient. For example, the device may provide a means of removing fragments of a kidney or gall stone from the body of a patient. In FIG. 5(A) the expandable portion 530 of device 500 is shown in a contracted state. In FIG. 5(B) the expandable portion 530 is shown in an expanded state.

Device 500 includes expandable portion 530 positioned at the distal end of elongated catheter 510. At least one optical fiber 520 extends from the proximal end 560 to the distal end 570 of elongated catheter 510. The proximal end of the at least one optical fiber is optically coupled to light source 550. Light source 550 may be, for example, a laser or a light emitting diode.

Expandable portion 530 includes a LASMP are disclosed herein. For example, the LASMP may be present at nodes positioned throughout the expandable portion as illustrated in FIGS. 1-4. The distal ends of optical fiber(s) 520 are optically coupled to the LASMP. Application of light to the proximal end of optical fiber(s) 520 results in the LASMP within expandable portion 530 changing state and the expandable portion 530 transforming from a collapsed state, as illustrated in FIG. 5(A) to an expanded state, as illustrated in FIG. 5(B). Then the light source is switch off, the expandable portion 530 will transform back to its collapsed configuration. In one embodiment, the size of holes 540 in expandable portion 530 increases when expandable portion 530 transforms from the collapsed to the expanded configuration.

Retrieval of Kidney or Other Stone Fragments

FIGS. 6(A-E) are schematic illustrations showing one embodiment of a method of retrieving kidney, or other, stone fragments from a body vessel utilizing an expandable device incorporating a light-activated shape-memory polymer. In many such procedures, the stone is fragmented before the stone fragments are removed from the urinary system.

Figure 6A:
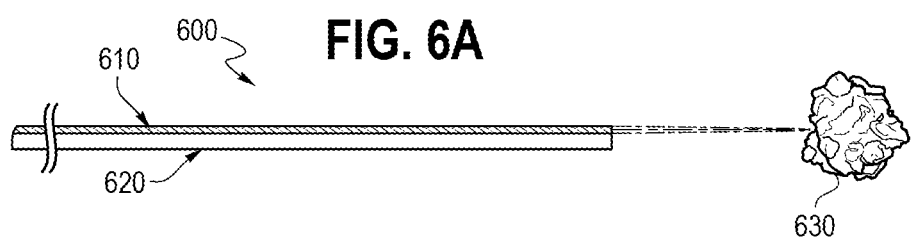
FIGS. 6(A-E) are schematic illustrations showing a method of retrieving kidney stone fragments from a body vessel utilizing an expandable device incorporating a light-activated shape-memory polymer In FIG. 6(A), the kidney stone is fragmented using a laser or other method.
In FIG. 6(B). the larger kidney stone fragments are removed from the urinary tract using a retrieval basket or similar device.
In FIG. 6(C), an expandable device having holes and including an expandable light-activated memory shape polymer is delivered to a region where smaller kidney stone fragments are still present. The device is delivered in a contracted state.
In FIG. 6(D), the device is expanded and the stone fragments enter the interior of the device.
In FIG. 6(E), the expandable device is collapsed, trapping the small kidney stone fragments. The device may then be removed from the vessel.

FIG. 6(A) shows kidney stone 630 and a distal portion of an implantable device 600 including an optical fiber 610 and a retrieval device 620. Optical fiber 610 may provide a means of delivering laser light to the kidney stone to fragment the stone into smaller fragments. In other embodiments, the stone is fragmented using a method such as sound wave illumination, percutaneous nephrolithotomy and the use of an ureterscope.

Figure 6B:
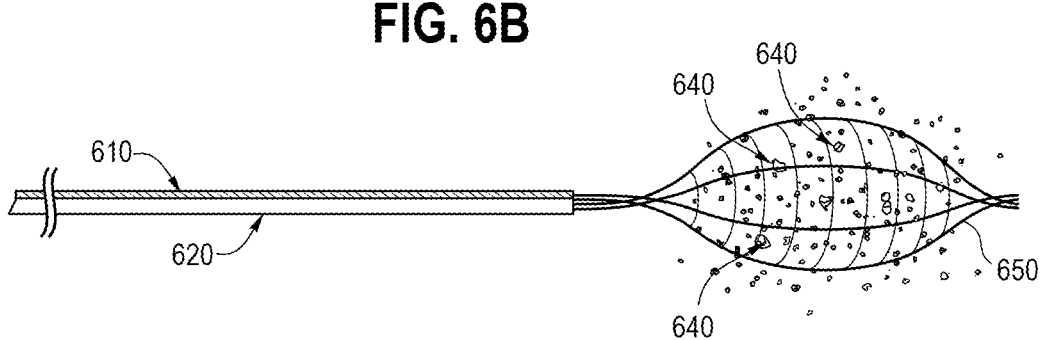

FIG. 6(B) illustrates the removal of the larger kidney stone fragments 640 from the urinary tract using retrieval basket or similar device 650. The larger fragments 650 are captured within the lumen of basket 650 and the retrieval, containing the captures fragments removed from the vessel. Fragments of the kidney stone that are too small for capture within the retrieval basket remain in the vessel after the removal of the retrieval device. Although such smaller fragments are too small to cause blockage of the vessel, they have the potential as acting a "seed crystals" and causing regrowth of the stone.

FIG. 6(C) illustrates a the delivery of device 656 to the region containing the small fragments 655. The device may be similar to the device described in FIGS. 5(A-B) and includes expandable portion 680. The expandable portion 680 includes LASMPs and is expandable when light is delivered to the LASMP through optical fiber 650.

Device 656 is delivered to the region containing the small stone fragments with expandable portion 680 in the collapsed configuration. When the device is in position, expandable position 680 is expanded, as illustrated in FIG. 6(D), so that the smaller stone fragments 655 are drawn into the interior of the expandable portion through pores 690. If necessary, fluid may be delivered to the region containing the fragments through flushing lumen 670. Stone fragments 655 may then be aspirated from the vessel through flushing lumen 670, or alternatively, through a separate lumen. During this process, expandable portion 680 provides support for the vessel wall and maintains the vessel in an open state.

Alter the stone fragments have been aspirated from the vessel, expandable portion 680 is returned to its collapsed state, as illustrated in FIG. 6(E), by turning off the light source. The device may then be removed from the vessel.

Bioactive Coated Devices

The expandable devices as disclosed herein may include a therapeutically effective amount of a bioactive agent. For example, the bioactive agent may be incorporated into, or coated onto, the expandable portion and/or another component of the device. For example, in the case of stent-graft devices, the bioactive agent may be incorporated into the woven or knitted graft material. In the case of stent devices, the bioactive material may be coated onto one or more surfaces of the stent.

The bioactive agent may be selected to perform a desired function upon implantation. Bioactive agents within the scope of the present embodiments include antiproliferative agents immunosuppressive agents, restenosis-inhibiting agents, anti-cancer agents, analgesics/antipyretics, anesthetics, antiasthmatics, antibiotics, antidepressants, antidiabetics, antifungal agents, antihypertensive agents, anti-inflammatories, antineoplastics, antianxiety agents, sedatives/hypnotics, antianginal agents, nitrates, antipsychotic agents, antimanic agents, antiarrhythmics, antiarthritic agents, antigout agents, thrombolytic agents, hemorheologic agents, anticonvulsants, antihistamines, agents useful for calcium regulation, antibacterial agents, antiviral agents, antimicrobials, anti-infectives, bronchodilators, steroids and hormones.

Non-limiting examples of such drugs include doxorubicin, camptothecin, etoposide, mitoxantrone, cyclosporine, epothilones, napthoquinones, 5 fluorouracil, methotrexate, colchicines, vincristine, vinblastine, gemcitabine, statins (for example atorvastatin, fluvastatin, lovastatin, pitavastatin, pravastatin, rosuvastatin and simvastatin), steroids (for example cortisteroids, prednisilone and dexamethazone) mitomycin and derivatives or analogues of these agents.

Preferred bioactive agents include restenosis-inhibiting agents a, including but not limited to microtubule stabilizing agent such as paclitaxel, a paclitaxel analog, or a paclitaxel derivative or other taxane compound; a macrolide immunosuppressive agent such as sirolimus (rapamycin), pimecrolimus, tacrolimus, everolimus, zotarolimus, novolimus, myolimus, temsirolimus, deforolimus, or biolimus; an antiproliferative agent; a smooth muscle cell inhibitor; an inhibitor of the mammalian target of rapamycin (mTOR inhibitor).

Certain bioactive agents may be present in more than one polymorphic form. For example, paclitaxel may be present as at one of Solid forms of amorphous paclitaxel ("aPTX"), dihydrate crystalline paclitaxel ("dPTX") and anhydrous crystalline paclitaxel.

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications as fall within the scope of the appended claims and equivalents thereof.

I claim:

1. An implantable medical device comprising:
an elongated catheter extending from a distal end to a proximal end and comprising a first lumen;
a plurality of optical fibers extending in the first lumen from the proximal end to the distal end;
an expandable body attaching to a distal end of the elongated catheter, wherein the expandable body comprises an light-sensitive polymeric material,
wherein a distal end of the plurality of optical fibers is optically coupled to the light-sensitive polymeric material,
wherein the expandable body comprises a hollow tubular body having a tubular wall comprising the light-sensitive polymeric material and defining an internal lumen, and
wherein the tubular wall comprises of plurality of interconnected segments, wherein each segment comprises a node point comprising the light-sensitive polymeric material.

2. The implantable medical device of claim 1, further comprising a light source optically coupled to a proximal end of the plurality of optical fibers.

3. The implantable medical device of claim 2, wherein the light source is selected from the group consisting of a laser and a light emitting diode.

4. The implantable medical device of claim 1, the expandable body having an expanded configuration and a collapsed configuration, wherein the expandable body transitions from the collapsed configuration to the expanded configuration upon optical illumination of the light-sensitive polymeric material.

5. The implantable medical device of claim 1, wherein the light-sensitive polymeric material comprises a polymer coupled to a material selected from the group consisting of cinnamic acid and cinnamylidene acetic acid.

6. The implantable medical device of claim 1, where at least one of the interconnected segments has expanded configuration and a collapsed configuration, wherein transition from the collapsed configuration to the expanded configuration comprises lengthening of the segment in a first direction without a change in dimension is a second perpendicular dimension.

7. The implantable medical device of claim 1, wherein the expandable body is selected from the group consisting of a balloon, a stent, a stent graft and a retrieval device.

8. The implantable medical device of claim 1, wherein the expandable body is a stent or a balloon.

9. The implantable medical device of claim 1, wherein the expandable body comprises a plurality of holes, wherein at least one of the plurality of holes increases in size upon expansion of the expandable body.

10. An implantable medical device comprising:
an elongated catheter comprising a first lumen;
a plurality of optical fibers extending from a proximal end to a distal end of the first lumen;
a light source optically coupled to a proximal end of the plurality of optical fibers;
an hollow expandable body having a plurality of holes and attaching to a distal end of the elongated catheter, wherein the expandable body comprises an light-sensitive polymeric material,
wherein a distal end of the plurality of optical fibers is optically coupled to the light-sensitive polymeric material,
wherein there are a plurality of light sources, and
wherein a first portion of the plurality of optical fibers is optically coupled to a first group of the plurality of light sources and to the light-sensitive polymeric material at a first region of the expandable body and wherein a second portion of the optical fibers is optically coupled to a second group of the plurality of light sources and to the light-sensitive polymeric material at a second region of the expandable body.

11. The implantable medical device of claim 10, further comprising a second lumen extending from a proximal end to a distal end of the elongated catheter.

12. The implantable medical device of claim 10, wherein the plurality of light sources are selected from the group consisting of a laser and a light emitting diode.

13. The implantable medical device of claim 10, wherein the implantable medical device comprises a balloon.

14. The implantable medical device kit of claim 10, wherein the light-sensitive polymeric material comprises a polymer coupled to a material selected from the group consisting of cinnamic acid and cinnamylidene acetic acid.

* * * * *